US010058262B2

(12) United States Patent
Briggs et al.

(10) Patent No.: US 10,058,262 B2
(45) Date of Patent: *Aug. 28, 2018

(54) SYSTEM AND METHOD OF IDENTIFYING SOURCES FOR BIOLOGICAL RHYTHMS

(71) Applicants: THE REGENTS OF THE UNIVERSITY OF CALIFORNIA, Oakland, CA (US); Topera, Inc., Menlo Park, CA (US)

(72) Inventors: Carey Robert Briggs, La Jolla, CA (US); Sanjiv M. Narayan, La Jolla, CA (US)

(73) Assignees: The Regents of the University of California, Oakland, CA (US); Topera, Inc., Menlo Park, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/194,357

(22) Filed: Jun. 27, 2016

(65) Prior Publication Data

US 2016/0324434 A1 Nov. 10, 2016

Related U.S. Application Data

(63) Continuation of application No. 13/470,705, filed on May 14, 2012, now Pat. No. 9,392,948.
(Continued)

(51) Int. Cl.
A61B 5/046 (2006.01)
A61B 5/0468 (2006.01)
(Continued)

(52) U.S. Cl.
CPC ............ *A61B 5/0468* (2013.01); *A61B 5/002* (2013.01); *A61B 5/042* (2013.01); *A61B 5/044* (2013.01);
(Continued)

(58) Field of Classification Search
CPC ... A61B 5/04012; A61B 5/0402; A61B 5/044; A61B 5/046; A61B 5/0464;
(Continued)

(56) References Cited

U.S. PATENT DOCUMENTS 4,421,114 A 12/1983 Berkovits et al.
4,630,204 A 12/1986 Mortara
(Continued)

FOREIGN PATENT DOCUMENTS

CN 1768342 A 5/2006
CN 101461711 A 6/2009
(Continued)

OTHER PUBLICATIONS

Censi et al. "Recurrent Patterns of Atrial Depolarization During Atrial Fibrillation Assessed by Recurrence Plot Quantification". Annals of Biomedical Engineering (2000) 28: 61.*
(Continued)

*Primary Examiner* — Eugene T Wu
(74) *Attorney, Agent, or Firm* — Eleanor Musick; Musick Davison, LLP

(57) ABSTRACT

In a system and method of determining regularity associated with a rhythm disorder of a heart, a derivative of a first cardiac signal at a plurality of first time points is processed against a derivative of a second cardiac signal at a plurality of second time points to define a plurality of coordinate pairs of the first cardiac signal against the second cardiac signal. Thereafter, an index of regularity that exceeds a threshold is determined. The index of regularity indicates an approxi-
(Continued)

mate congruence of the plurality of coordinate pairs among the first cardiac signal and the second cardiac signal.

27 Claims, 10 Drawing Sheets
(3 of 10 Drawing Sheet(s) Filed in Color)

Related U.S. Application Data

(60) Provisional application No. 61/569,132, filed on Dec. 9, 2011.

(51) Int. Cl.
  *A61B 5/00*     (2006.01)
  *A61B 5/044*    (2006.01)
  *A61B 5/042*    (2006.01)
  *A61B 5/04*     (2006.01)
  *A61B 5/0452*   (2006.01)
  *A61B 8/02*     (2006.01)
  *A61B 5/0464*   (2006.01)
  *A61B 5/024*    (2006.01)

(52) U.S. Cl.
  CPC .......... *A61B 5/046* (2013.01); *A61B 5/04011* (2013.01); *A61B 5/04012* (2013.01); *A61B 5/0422* (2013.01); *A61B 5/0452* (2013.01); *A61B 5/7239* (2013.01); *A61B 5/7246* (2013.01); *A61B 5/7257* (2013.01); *A61B 8/02* (2013.01); *A61B 5/02405* (2013.01); *A61B 5/0464* (2013.01); *A61B 5/04525* (2013.01); *A61B 5/743* (2013.01); *A61B 5/7425* (2013.01)

(58) Field of Classification Search
  CPC ... A61B 5/6869; A61B 5/7235; A61B 5/7239; A61B 5/7246; A61B 5/7253; A61B 5/7257; A61B 5/7271; A61B 5/7275; A61B 5/7282; A61B 5/7425; A61B 5/743
  See application file for complete search history.

(56) References Cited

U.S. PATENT DOCUMENTS

| | | | |
|---|---|---|---|
| 4,754,763 A * | 7/1988 | Doemland | A61B 5/4504 600/552 |
| 4,905,707 A * | 3/1990 | Davies | A61B 5/0006 600/515 |
| 4,905,708 A * | 3/1990 | Davies | A61B 5/7239 600/518 |
| 5,029,082 A | 7/1991 | Shen et al. | |
| 5,092,341 A | 3/1992 | Kelen | |
| 5,121,750 A | 6/1992 | Katims | |
| 5,172,699 A | 12/1992 | Svenson et al. | |
| 5,178,154 A | 1/1993 | Ackmann et al. | |
| 5,366,487 A | 11/1994 | Adams et al. | |
| 5,427,112 A | 6/1995 | Noren et al. | |
| 5,433,198 A | 7/1995 | Desai | |
| 5,439,483 A | 8/1995 | Duong-Van | |
| 5,450,846 A | 9/1995 | Goldreyer | |
| 5,458,621 A | 10/1995 | White et al. | |
| 5,480,422 A | 1/1996 | Ben-Haim | |
| 5,487,391 A | 1/1996 | Panescu | |
| 5,582,173 A | 12/1996 | Li | |
| 5,645,070 A | 7/1997 | Turcott | |
| 5,657,755 A | 8/1997 | Desai | |
| 5,662,108 A | 9/1997 | Budd et al. | |
| 5,687,737 A | 11/1997 | Branham et al. | |
| 5,718,241 A | 2/1998 | Ben-Haim et al. | |
| 5,795,303 A | 8/1998 | Swanson et al. | |
| 5,810,740 A | 9/1998 | Paisner | |
| 5,817,134 A | 10/1998 | Greenhut et al. | |
| 5,819,740 A | 10/1998 | Muhlenberg | |
| 5,836,889 A | 11/1998 | Wyborny et al. | |
| 5,840,025 A | 11/1998 | Ben-Haim | |
| 5,848,972 A | 12/1998 | Triedman et al. | |
| 5,868,680 A | 2/1999 | Steiner et al. | |
| 5,954,661 A | 9/1999 | Greenspan et al. | |
| 5,954,665 A | 9/1999 | Ben-Haim | |
| 6,052,618 A | 4/2000 | Dahlke et al. | |
| 6,066,094 A | 5/2000 | Ben-Haim | |
| 6,097,983 A * | 8/2000 | Strandberg | A61B 5/0452 600/518 |
| 6,112,117 A | 8/2000 | Kenknight et al. | |
| 6,115,628 A | 9/2000 | Stadler et al. | |
| 6,188,924 B1 | 2/2001 | Swanson et al. | |
| 6,208,888 B1 | 3/2001 | Yonce | |
| 6,236,883 B1 | 5/2001 | Ciaccio et al. | |
| 6,251,125 B1 | 6/2001 | Kenknight et al. | |
| 6,256,540 B1 | 7/2001 | Panescu et al. | |
| 6,301,496 B1 | 10/2001 | Reisfeld | |
| 6,324,421 B1 | 11/2001 | Stadler et al. | |
| 6,360,121 B1 | 3/2002 | Shoda et al. | |
| 6,397,100 B2 | 5/2002 | Stadler et al. | |
| 6,438,406 B2 | 8/2002 | Yonce | |
| 6,438,409 B1 | 8/2002 | Malik et al. | |
| 6,449,503 B1 | 9/2002 | Hsu | |
| 6,510,339 B2 | 1/2003 | Kovtun et al. | |
| 6,522,905 B2 | 2/2003 | Desai | |
| 6,539,256 B1 | 3/2003 | Kenknight et al. | |
| 6,542,773 B2 | 4/2003 | Dupree et al. | |
| 6,553,251 B1 * | 4/2003 | Lahdesmaki | A61B 5/0006 600/519 |
| 6,584,345 B2 | 6/2003 | Govari | |
| 6,725,085 B2 | 4/2004 | Schwartzman et al. | |
| 6,738,655 B1 | 5/2004 | Sen et al. | |
| 6,788,969 B2 | 9/2004 | Dupree et al. | |
| 6,847,839 B2 * | 1/2005 | Ciaccio | A61B 5/04011 600/512 |
| 6,856,830 B2 | 2/2005 | He | |
| 6,889,081 B2 | 5/2005 | Hsu | |
| 6,892,091 B1 | 5/2005 | Ben-Haim et al. | |
| 6,920,350 B2 | 7/2005 | Xue et al. | |
| 6,941,166 B2 | 9/2005 | MacAdam et al. | |
| 6,950,696 B2 | 9/2005 | Bjorling et al. | |
| 6,950,702 B2 | 9/2005 | Sweeney | |
| 6,959,212 B2 | 10/2005 | Hsu et al. | |
| 6,975,900 B2 | 12/2005 | Rudy et al. | |
| 6,978,168 B2 | 12/2005 | Beatty et al. | |
| 6,985,768 B2 | 1/2006 | Hemming et al. | |
| 7,016,719 B2 | 3/2006 | Rudy et al. | |
| 7,043,292 B2 | 5/2006 | Tarjan et al. | |
| 7,076,288 B2 | 7/2006 | Skinner | |
| 7,117,030 B2 | 10/2006 | Berenfeld et al. | |
| 7,123,954 B2 | 10/2006 | Narayan et al. | |
| 7,206,630 B1 | 4/2007 | Tarler | |
| 7,215,993 B2 | 5/2007 | Lin | |
| 7,245,962 B2 | 7/2007 | Ciaccio et al. | |
| 7,263,397 B2 | 8/2007 | Hauck et al. | |
| 7,283,865 B2 | 10/2007 | Noren | |
| 7,289,843 B2 | 10/2007 | Beatty et al. | |
| 7,289,845 B2 | 10/2007 | Sweeney et al. | |
| 7,328,063 B2 | 2/2008 | Zhang et al. | |
| 7,369,890 B2 | 5/2008 | Lovett | |
| 7,505,810 B2 | 3/2009 | Harlev et al. | |
| 7,515,954 B2 | 4/2009 | Harlev et al. | |
| 7,567,835 B2 | 7/2009 | Gunderson et al. | |
| 7,580,744 B2 | 8/2009 | Hsu | |
| 7,620,446 B2 | 11/2009 | Ferek-Petric | |
| 7,657,307 B2 | 2/2010 | Dam et al. | |
| 7,729,753 B2 | 6/2010 | Kremliovsky et al. | |
| 7,734,333 B2 | 6/2010 | Ghanem et al. | |
| 7,734,336 B2 | 6/2010 | Ghanem et al. | |
| 7,738,948 B2 | 6/2010 | Rouw et al. | |
| 7,742,812 B2 | 6/2010 | Ghanem et al. | |
| 7,751,882 B1 | 7/2010 | Helland | |
| 7,761,142 B2 | 7/2010 | Ghanem et al. | |
| 7,761,150 B2 | 7/2010 | Ghanem et al. | |
| 7,769,452 B2 | 8/2010 | Ghanem et al. | |
| 7,801,594 B1 | 9/2010 | Higham | |
| 7,907,993 B2 | 3/2011 | Ghanem et al. | |

(56) References Cited

U.S. PATENT DOCUMENTS

| | | |
|---|---|---|
| 7,907,994 B2 * | 3/2011 | Stolarski .......... A61B 5/04525 600/515 |
| 7,930,018 B2 | 4/2011 | Harley et al. |
| 7,930,020 B2 | 4/2011 | Zhang et al. |
| 7,953,475 B2 | 5/2011 | Harley et al. |
| 7,962,202 B2 | 6/2011 | Bhunia |
| 8,050,732 B2 | 11/2011 | Desai |
| 8,050,751 B2 | 11/2011 | Zhang et al. |
| 8,050,757 B2 | 11/2011 | Hsu |
| 8,095,205 B2 | 1/2012 | Bhunia |
| 8,095,206 B2 | 1/2012 | Ghanem et al. |
| 8,160,684 B2 | 4/2012 | Ghanem et al. |
| 8,165,666 B1 | 4/2012 | Briggs et al. |
| 8,165,671 B2 | 4/2012 | Freeman et al. |
| 8,175,702 B2 | 5/2012 | Efimov et al. |
| 8,306,618 B2 | 11/2012 | Ghanem et al. |
| 8,315,697 B2 | 11/2012 | Hsu |
| 8,340,766 B2 | 12/2012 | Ryu et al. |
| 8,386,024 B2 | 2/2013 | Gunderson et al. |
| 8,435,185 B2 | 5/2013 | Ghanem et al. |
| 8,489,171 B2 | 7/2013 | Hauck et al. |
| 8,521,266 B2 | 8/2013 | Narayan et al. |
| 8,588,885 B2 | 11/2013 | Hall et al. |
| 8,594,777 B2 * | 11/2013 | Briggs ............ A61B 5/0422 600/515 |
| 8,639,325 B2 | 1/2014 | Efimov et al. |
| 8,676,303 B2 | 3/2014 | Narayan |
| 8,700,140 B2 | 4/2014 | Narayan et al. |
| 8,715,199 B1 | 5/2014 | Macneil et al. |
| 8,812,074 B2 | 8/2014 | Kordis et al. |
| 8,838,222 B2 | 9/2014 | Narayan et al. |
| 8,838,223 B2 | 9/2014 | Narayan et al. |
| 8,868,169 B2 | 10/2014 | Narayan et al. |
| 9,031,642 B2 * | 5/2015 | Ghosh ............ A61B 5/7246 600/509 |
| 9,050,006 B2 | 6/2015 | Narayan et al. |
| 9,055,876 B2 | 6/2015 | Narayan et al. |
| 9,055,877 B2 | 6/2015 | Narayan et al. |
| 9,055,878 B2 | 6/2015 | Narayan et al. |
| 9,089,269 B2 | 7/2015 | Narayan et al. |
| 9,107,600 B2 | 8/2015 | Narayan et al. |
| 9,220,427 B2 | 12/2015 | Narayan et al. |
| 9,241,667 B2 | 1/2016 | Narayan et al. |
| 9,282,910 B2 | 3/2016 | Narayan et al. |
| 9,332,915 B2 | 5/2016 | Narayan et al. |
| 9,375,156 B2 | 6/2016 | Narayan et al. |
| 9,380,950 B2 | 7/2016 | Narayan et al. |
| 9,393,425 B2 | 7/2016 | Narayan |
| 9,398,860 B2 | 7/2016 | Macneil et al. |
| 9,398,883 B2 | 7/2016 | Narayan et al. |
| 9,408,536 B2 | 8/2016 | Narayan et al. |
| 9,439,573 B2 | 9/2016 | Narayan et al. |
| 9,468,387 B2 | 10/2016 | Narayan et al. |
| 9,549,684 B2 | 1/2017 | Narayan et al. |
| 9,668,666 B2 | 6/2017 | Narayan et al. |
| 2002/0016548 A1 * | 2/2002 | Stadler ............ A61B 5/04011 600/509 |
| 2003/0018277 A1 | 1/2003 | He |
| 2003/0083587 A1 | 5/2003 | Ferek-Petric |
| 2004/0059237 A1 * | 3/2004 | Narayan .......... A61B 5/04525 600/509 |
| 2004/0093035 A1 * | 5/2004 | Schwartz ........... A61N 1/3956 607/5 |
| 2004/0243014 A1 * | 12/2004 | Lee ................ A61B 5/04525 600/510 |
| 2005/0027321 A1 | 2/2005 | Ferek-Petric |
| 2005/0137638 A1 * | 6/2005 | Yonce ............. A61N 1/3712 607/28 |
| 2005/0203502 A1 | 9/2005 | Boveja et al. |
| 2006/0161069 A1 * | 7/2006 | Li ................ A61B 5/04525 600/515 |
| 2007/0016261 A1 * | 1/2007 | Dong ............. A61B 5/04525 607/28 |
| 2007/0055167 A1 | 3/2007 | Bullinga |
| 2007/0208260 A1 | 9/2007 | Afonso |
| 2007/0208263 A1 | 9/2007 | John et al. |
| 2007/0232948 A1 | 10/2007 | Stadler et al. |
| 2007/0239051 A1 | 10/2007 | Ghanem et al. |
| 2007/0299351 A1 | 12/2007 | Harley et al. |
| 2008/0097539 A1 | 4/2008 | Belalcazar |
| 2008/0109041 A1 | 5/2008 | de Voir |
| 2008/0114258 A1 | 5/2008 | Zhang et al. |
| 2008/0208012 A1 * | 8/2008 | Ali ............... G06Q 50/22 600/301 |
| 2008/0269624 A1 | 10/2008 | Zhang et al. |
| 2009/0069704 A1 | 3/2009 | MacAdam et al. |
| 2009/0099468 A1 | 4/2009 | Thiagalingam et al. |
| 2009/0099618 A1 * | 4/2009 | Rousso ........... A61B 5/04525 607/25 |
| 2009/0112106 A1 | 4/2009 | Zhang |
| 2009/0112110 A1 | 4/2009 | Zhang |
| 2009/0112199 A1 | 4/2009 | Zhang et al. |
| 2009/0131760 A1 | 5/2009 | Ali et al. |
| 2009/0163968 A1 | 6/2009 | Donofrio |
| 2009/0259266 A1 | 10/2009 | Zhang et al. |
| 2009/0299203 A1 | 12/2009 | de Voir et al. |
| 2010/0026543 A1 | 2/2010 | Tsai et al. |
| 2010/0204592 A1 | 8/2010 | Hatib et al. |
| 2010/0217143 A1 | 8/2010 | Whittington et al. |
| 2010/0239627 A1 | 9/2010 | Whitekettle et al. |
| 2010/0249627 A1 | 9/2010 | Zhang et al. |
| 2010/0298729 A1 | 11/2010 | Zhang et al. |
| 2010/0305456 A1 | 12/2010 | Brainard, II |
| 2010/0324435 A1 | 12/2010 | Higham |
| 2011/0077540 A1 | 3/2011 | Belalcazar |
| 2011/0087121 A1 | 4/2011 | Zhang et al. |
| 2011/0112425 A1 | 5/2011 | Muhlsteff et al. |
| 2011/0130801 A1 | 6/2011 | Maskara et al. |
| 2011/0196249 A1 | 8/2011 | Staeuber et al. |
| 2011/0257547 A1 | 10/2011 | Zhang |
| 2011/0282227 A1 | 11/2011 | Zhang |
| 2012/0184858 A1 | 7/2012 | Harley et al. |
| 2012/0232417 A1 | 9/2012 | Zhang |
| 2013/0245474 A1 * | 9/2013 | Nicolson ........... A61B 5/0464 600/518 |
| 2013/0324871 A1 | 12/2013 | Dubois et al. |
| 2013/0345577 A1 | 12/2013 | Thakur et al. |
| 2014/0005562 A1 | 1/2014 | Bunch et al. |
| 2014/0049402 A1 | 2/2014 | Beaulieu et al. |
| 2014/0336520 A1 | 11/2014 | Zeng et al. |
| 2014/0371609 A1 | 12/2014 | Narayan et al. |
| 2014/0371613 A1 | 12/2014 | Narayan et al. |
| 2016/0015283 A1 | 1/2016 | Narayan et al. |
| 2016/0022163 A1 | 1/2016 | Narayan et al. |
| 2016/0166167 A1 | 6/2016 | Narayan et al. |
| 2016/0262643 A1 * | 9/2016 | Ng ................ A61B 5/7246 |
| 2016/0278657 A1 | 9/2016 | Narayan et al. |
| 2016/0302734 A1 | 10/2016 | Narayan |
| 2016/0360983 A1 | 12/2016 | Narayan et al. |
| 2016/0374571 A1 | 12/2016 | Narayan et al. |
| 2017/0007176 A1 | 1/2017 | Narayan et al. |

FOREIGN PATENT DOCUMENTS

| | | |
|---|---|---|
| EP | 2269691 A2 | 1/2011 |
| EP | 1808124 B1 | 4/2011 |
| JP | H09215667 | 8/1997 |
| WO | 1994021168 A1 | 9/1994 |
| WO | 1996025096 A1 | 8/1996 |
| WO | 1996032885 A1 | 10/1996 |
| WO | 1996032897 A1 | 10/1996 |
| WO | 1996039929 A1 | 12/1996 |
| WO | 1997024983 A2 | 7/1997 |
| WO | 2000045700 A1 | 8/2000 |
| WO | 2003011112 A2 | 2/2003 |
| WO | 2005035046 A2 | 4/2005 |
| WO | 2005115232 A1 | 12/2005 |
| WO | 2006052838 A2 | 5/2006 |
| WO | 2006066324 A1 | 6/2006 |
| WO | 2007078421 A2 | 7/2007 |
| WO | 2007106829 A2 | 9/2007 |
| WO | 2007137077 A2 | 11/2007 |

(56) References Cited

FOREIGN PATENT DOCUMENTS

| WO | 2007146864 A2 | 12/2007 |
|---|---|---|
| WO | 2008035070 A2 | 3/2008 |
| WO | 2008138009 A1 | 11/2008 |

OTHER PUBLICATIONS

G. W. Botteron and J. M. Smith, "A technique for measurement of the extent of spatial organization of atrial activation during atrial fibrillation in the intact human heart," in IEEE Transactions on Biomedical Engineering, vol. 42, No. 6, pp. 579-586, Jun. 1995.*
Ciaccio, Edward J. et al., "Development of Gradient Descent Adaptive Algorithms to Remove Common Mode Artifact for Improvement of Cardiovascular Signal Quality", Annals of Biomedical Engineering, vol. 35, No. 7, Jul. 2007, pp. 1146-1155.
Eckman, et al. "Recurrence plots of dynamical systems," Europhys. Lett., 4 (3), Nov. 1, 1987 pp. 973-977.
English-language translation of Chinese patent publication No. CN 101461711A, published Jun. 24, 2009.
EP09819953 Supplementary European Search Report & European Search Opinion dated Feb. 7, 2012, 12 pages.
EP12711553 Supplementary European Search Report & European Search Opinion , dated Sep. 11, 2013, 7 pages.
EP12779506.0 Supplementary European Search Report & European Search Opinion dated Nov. 18, 2014, 8 pages.
EP12855266.8: Supplementary European Search Report & European Search Opinion, dated Jun. 2, 2015, 9 pages.
EP12855738.6: Supplementary European Search Report & European Search Opinion, dated Jun. 5, 2015, 9 pages.
EP14763969.4 Supplementary European Search Report & European Search Opinion dated Oct. 21, 2016, 7 pages.
EP147665096.4 Supplementary European Search Report & European Search Opinion, dated Oct. 21, 2016, 6 pages.
EP15192804.1 Supplementary European Search Report, dated Feb. 18, 2016, 7 pages.
Holm, M. et al., "A New Method for Analysis of Atrial Activation During Chronic Atrial Fibrillation in Man", IEEE Transactions on Biomedical Engineering, vol. 43, No. 2, Feb. 1, 1996, pp. 198-210.
Houben, R.P.M., et al, "Automatic mapping of human atrial fibrillation by template matching", Heart Rhythm, vol. 3, No. 10, Oct. 1, 2006, pp. 1221-1228.
Houben, R.P.M., et al., "Processing of Intracardiac Electrograms in Atrial Fibrillation", IEEE Engineering in Medicine and Biology Magazine, Nov./Dec. 2006, pp. 40-51.
Jung, TP et al, Removing Electroencephalographic Artifacts by Blind Source Separation, Psychophysiology, 37.02 (2000): 163-178.
Kadish, A., et al., "Characterization of fibrillatory rhythms by ensemble vector directional analysis", Am J Physiol.—Heart Circ. Physiol., vol. 285, Oct. 2003, pp. H1705-H1719.
Kalifa, J, et al. "Mechanisms of wave fractionation at boundaries of high-frequency excitation in the posterior left atrium of the isolated sheep heart during atrial fibrillation," Circulation, vol. 113, No. 5, Feb. 7, 2006, pp. 626-633.
Lin, Y-J, et al., "Electrophyiological Characteristics and Catheter Ablation in Patients With Paroxysmal Right Atrial Fibrillation", Circulation, Sep. 20, 2005; 112(12): 1692-1700, EPub Sep. 12, 2005.

Masse, S., et al., "Wave similarity of human ventricular fibrillation from bipolar electrograms", Eurospace (2007) vol. 9, pp. 10-19.
Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.
Narayan, S.M., et al., "Dynamics factors preceding the initiation of atrial fibrillation in humans", Heart Rhythm, vol. 5, No. 6, Jun. 1, 2008, pp. S22-S25.
PCT/US2009/060178 International Preliminary Report on Patentability and Written Opinion, dated Apr. 12, 2011, 10 pages.
PCT/US2011/031468 International Preliminary Report on Patentability and Written Opinion, dated Oct. 9, 2012, 8 pages.
PCT/US2011/031470 International Preliminary Report on Patentability and Written Opinion, dated Oct. 9, 2012, 7 pages.
PCT/US2012/029935 International Search Report and Written Opinion, dated Nov. 8, 2012, 9 pages.
PCT/US2012/036157 International Preliminary Report on Patentability and Written Opinion, dated Aug. 14, 2012, 8 pages.
PCT/US2012/068639 International Preliminary Report on Patentability and Written Opinion, dated Jun. 10, 2013; 6 pages.
PCT/US2012/068640 International Preliminary Report on Patentability and Written Opinion, dated Jun. 10, 2013; 5 pages.
PCT/US2014/029616 International Search Report and Written Opinion, dated Sep. 18, 2014; 9 pages.
PCT/US2014/029645 International Search Report and Written Opinion, dated Aug. 18, 2014, 17 pages.
PCT/US2015/023929, International Search Report and Written Opinion, dated Jul. 9, 2015, 8 pages.
PCT/US2015/046742 International Search Report and Written Opinion; dated Dec. 1, 2015, 5 pages.
Saksena, S., et al., "Regional Endocardial Mapping of Spontaneous and Induced Atrial Fibrillation in Patients With Heart Disease and Refractory Atrial Fibrillation", Am J Cardiol, 1999; 84:880-889.
Sornborger, Andrew, et al., "Extraction of Periodic Multivariate Signals: Mapping of Voltage-Dependent Dye Fluorescence in the Mouse Heart", IEEE Transactions on Medical Imaging, vol. 22, No. 12, Dec. 2003, pp. 1537-1549.
Sun, Yan, et al., "Characteristic wave detection in ECG signal using morphological transform", BMC Cardiovascular Disorders, vol. 5, No. 28, 2005, 7 pages.
Tai, Dean C.S., et al., "Correction of motion artifact in transmembrane voltage-sensitive fluorescent dye emission in hearts", Am. J. Physiol. Heart Circ. Physiol., vol. 287, 2004, pp. H985-H993.
Ulphani, J.S., et al., "Frequency gradients during two different forms of fibrillation in canine atria", Heart Rhythm, vol. 4, No. 10, Oct. 2007, pp. 1315-1323.
Umapathy, K, et al. "Spatiotemporal Frequency Analysis of Ventricular Fibrillation in Explanted Human Hearts," IEEE Transactions in Biomedical Engineering, IEEE Service Center, Piscataway, NJ USA, vol. 56, No. 2, Feb. 1, 2009, pp. 238-335.
Yenn-Jiang L, et al. "Electrophysiological Mechanisms and Catheter Ablation of Complex Atrial Arrhythmias from Crista Terminalis: Insight from Three-Dimentional Noncontact Mapping," Pacing and Clinical Electrophysiology, vol. 27, No. 9, Sep. 1, 2004, pp. 1231-1239.

* cited by examiner

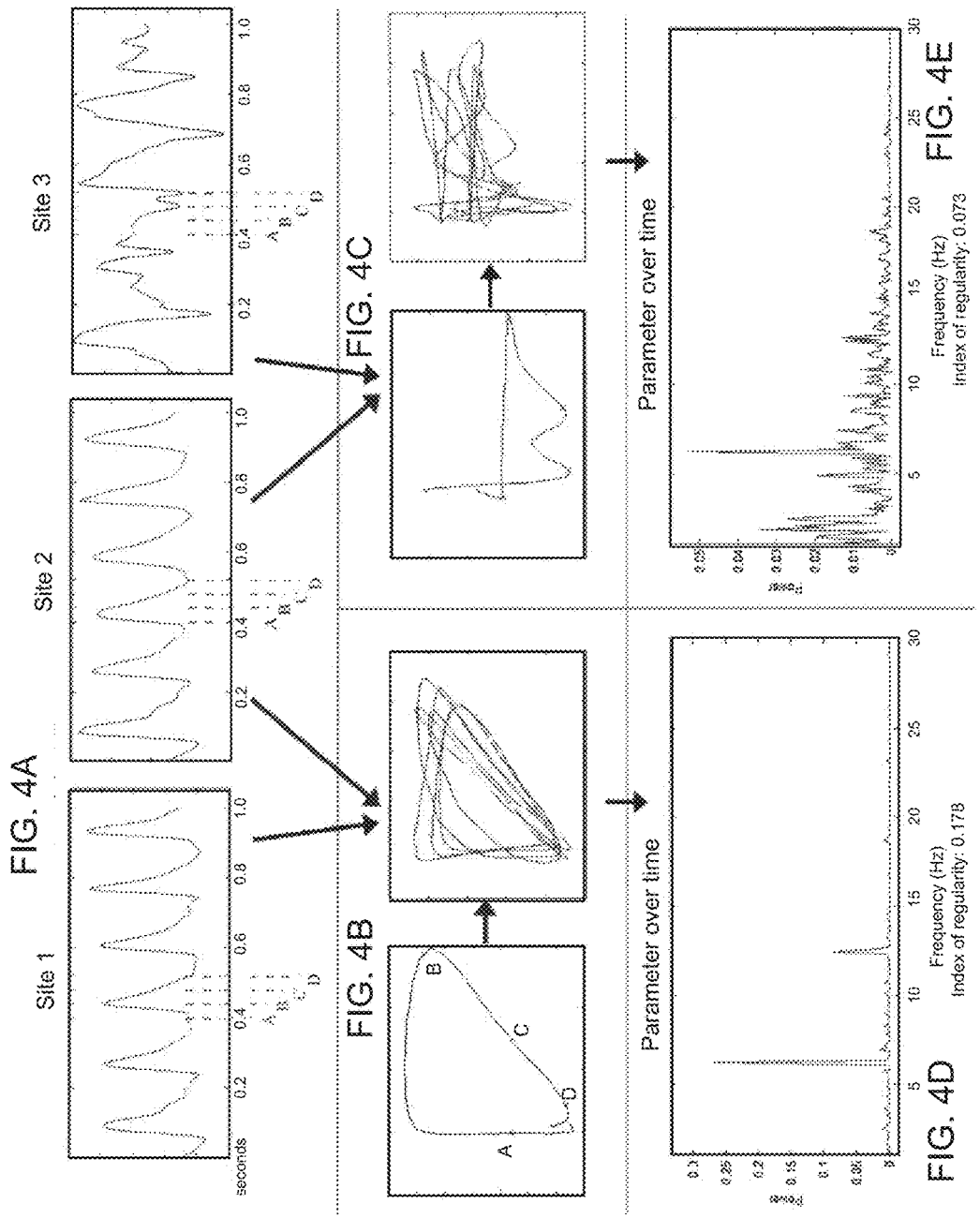

Successful site of ablation

SYSTEM AND METHOD OF IDENTIFYING SOURCES FOR BIOLOGICAL RHYTHMS

RELATED APPLICATIONS

This application is a continuation of U.S. application Ser. No. 13/470,705, filed May 14, 2012, issued as U.S. Pat. No. 9,392,948, which claims priority to U.S. Provisional Application No. 61/569,132 filed Dec. 9, 2011, each of which is incorporated herein by reference in its entirety.

GOVERNMENT RIGHTS

This invention was made with government support under Grants HL83359 and HL103800 awarded by the National Institutes of Health (NIH). The government has certain rights in the invention.

BACKGROUND

Field

The present application relates generally to biological rhythm disorders. More specifically, the present application is directed to a system and method of identifying one or more sources of a biological rhythm disorder, such as a heart rhythm disorder.

Related Art

Heart rhythm disorders are common and represent significant causes of morbidity and death throughout the world. Malfunction of the electrical system in the heart represents a proximate cause of heart rhythm disorders. Heart rhythm disorders exist in many forms, of which the most complex and difficult to treat are atrial fibrillation (AF), ventricular tachycardia (VT) and ventricular fibrillation (VF). Other rhythm disorders are more simple to treat, but may also be clinically significant including atrial tachycardia (AT), supraventricular tachycardia (SVT), atrial flutter (AFL), premature atrial complexes/beats (SVE) and premature ventricular complexes/beats (PVC). While under normal conditions the sinus node keeps the heart in sinus rhythm, under certain conditions rapid activation of the normal sinus node can cause inappropriate sinus tachycardia or sinus node reentry, both of which also represent heart rhythm disorders.

Treatment of heart rhythm disorders—particularly complex rhythm disorders of AF, VF and VT—can be very difficult. Pharmacologic therapy for complex rhythm disorder is not optimal. Ablation has been used increasingly in connection with heart rhythm disorders by maneuvering a sensor/probe to the heart through the blood vessels, or directly at surgery, and delivering energy to a location of the heart to mitigate and in some cases to eliminate the heart rhythm disorder. However, in complex rhythm disorders ablation is often difficult and ineffectual because tools that identify and locate a cause (source) of the heart rhythm disorder are poor and hinder attempts to deliver energy to a correct region of the heart to eliminate the disorder.

Certain systems and methods are known for treating simple heart rhythm disorders. In a simple heart rhythm disorder (e.g., atrial tachycardia), the source of the disorder can be identified by tracing activation back to the earliest location, which can be ablated to mitigate and in some cases to eliminate the disorder. Even in simple heart rhythm disorders, ablating the cause of a heart rhythm disorder is challenging and experienced practitioners often require hours to ablate simple rhythm disorders with consistent beat-to-beat activation patterns, such as atrial tachycardia.

There are few, if any, known systems and methods that have been successful with respect to identifying the sources or causes for complex rhythm disorders such as AF, VF or polymorphic VT. In a complex rhythm disorder, an earliest location of activation onsets cannot be identified because activation onset patterns change from beat to beat.

Diagnosing and treating heart rhythm disorders generally involves the introduction of a catheter having a plurality of sensors/probes into the heart through blood vessels of a patient. The sensors detect electric activity of the heart at sensor locations in the heart. The electric activity is generally processed into electrogram signals that represent the activation of the heart at the sensor locations.

In a simple heart rhythm disorder, the signal at each sensor location is generally consistent from beat to beat, enabling identification of the earliest activation. However, in a complex rhythm disorder, the signal at each sensor location from beat to beat may transition between one, several, and multiple deflections of various shapes. For instance, when a signal for a sensor location in AF includes 5, 7, 11 or more deflections, it is difficult if not impossible to identify which deflections in the signal are local to the sensor location in the heart (i.e., local activation onset) versus a nearby sensor location in the heart (i.e., far-field activation onset) or simply noise from another part of the patient's heart, other anatomic structures or external electronic systems. The foregoing deflections make it difficult if not impossible to identify activation onset times of the beats in a signal at a sensor location.

There are no known systems and methods that have been able to identify the source (or sources) for a heart rhythm disorder independently of identifying and assigning activation onset times to signals of successive beats. Given the difficulties in identifying the activation onset times, this has significantly limited diagnosis of the source (or sources) of heart rhythm disorders, especially for complex rhythm disorders, and has limited treatment attempts at their elimination.

BRIEF SUMMARY

The present invention is applicable to identifying sources of various rhythms, including normal and disordered heart rhythms, as well as other biological rhythms and rhythm disorders, such as neurological seizures, esophageal spasms, bladder instability, irritable bowel syndrome, and other biological disorders for which biological signals can be recorded to permit determination, diagnosis, and/or treatment of the cause (or source) of the disorders. The invention does not rely on or calculate the onset of activation in signals at any sensor locations, and thus it is particularly useful in complex rhythm disorders which provide complex activation patterns and complex varying beat signals. It is especially useful in identifying the cause(s) of the disorders of heart rhythm such that they can be treated with expediency.

Complex heart rhythm disorders typically result in an array of activation patterns that are extremely difficult to decipher, so that the ability to determine accurate activation of a heart beat has previously not been possible. Among the advantages of the present invention is the ability to identify a source of a complex rhythm disorder from regularity in signals at sensor locations relative to signals at adjacent sensor locations, independently of the assignment of specific activation onset times (identifying beats) in signals at these sensor locations. In this way, the invention enables a determination of a source (or sources) of the heart rhythm disorder for treatment. Another advantage is that the present invention provides a method and system which can be carried out rapidly while a sensing device—such as a catheter having sensors thereon—is used in or near the patient and is followed by treatment of cardiac tissue to ameliorate the disorder and in many cases to cure the disorder. Treatment may thus occur immediately, since the invention will provide the location(s) of the source of the heart rhythm disorder.

Prior methods and systems suffered from the inability to determine the source of rhythm disorders and consequently provided no means of targeting the source for meaningful and curative treatment. Additionally, prior methods and systems required numerous and complex steps of treatment and yet still failed to provide a means of determining the source(s) of heart rhythm disorders. In contrast, the present invention provides a relatively few number of steps to determine the source(s) for a heart rhythm disorder, including complex rhythm disorders of atrial and ventricular fibrillation.

In accordance with an embodiment, a system to measure regularity associated with a heart rhythm is disclosed. The system includes at least one computing device. The at least one computing device is configured to process a derivative of a first cardiac signal at a plurality of first time points against a derivative of a second cardiac signal at a plurality of second time points to define a plurality of coordinate pairs of the first cardiac signal against the second cardiac signal. The at least one computing device is further configured to determine an index of regularity that exceeds a threshold, the index of regularity indicating an approximate congruence of the plurality of coordinate pairs among the first cardiac signal and the second cardiac signal.

The at least one computing device is further configured to iteratively select pairs of cardiac signals from a plurality of cardiac signals, each pair having a first cardiac signal and different second cardiac signal. The at least one computing device is also configured to perform the processing and determining for each pair of the iteratively selected pairs of cardiac signals. The at least one computing device is further configured to construct a matrix of indexes of regularity for the iteratively selected pairs of cardiac signals, and to determine one or more sources of the rhythm disorder using the matrix of indexes of regularity.

In order to determine the one or more sources of the rhythm disorder, the at least one computing device is configured to identify from the matrix one or more regions of the heart associated with high indexes of regularity as compared to indexes of regularity at adjacent regions of the heart.

In accordance with another embodiment, a method of measuring regularity associated with a rhythm disorder of a heart. The method includes processing by a computing device a derivative of a first cardiac signal at a plurality of first time points against a derivative of a second cardiac signal at a plurality of second time points to define a plurality of coordinate pairs of the first cardiac signal against the second cardiac signal. The method further includes determining by the computing device an index of regularity that exceeds a threshold, the index of regularity indicating an approximate congruence of the plurality of coordinate pairs among the first cardiac signal and the second cardiac signal.

The method further comprises iteratively selecting pairs of cardiac signals from a plurality of cardiac signals, each pair having a first cardiac signal and different second cardiac signal. The method also includes performing the processing and determining for each pair of the iteratively selected pairs of cardiac signals. The method further includes constructing a matrix of indexes of regularity for the iteratively selected pairs of cardiac signals, and determining one or more sources of the rhythm disorder using the matrix of indexes of regularity.

In order to determine the one or more sources of the rhythm disorder, the method further includes identifying from the matrix one or more regions of the heart associated with high indexes of regularity as compared to indexes of regularity at adjacent regions of the heart.

In accordance with a further embodiment, a method of treating a cardiac rhythm disorder is provided. The method includes iteratively selecting pairs of cardiac signals from a plurality of cardiac signals, each pair having a first cardiac signal and different second cardiac signal. The method further includes processing a derivative of the first cardiac signal at a plurality of first time points against a derivative of the different second cardiac signal at a plurality of second time points to define a plurality of coordinate pairs of the first cardiac signal against the different second cardiac signal for each selected pair. Thereafter, the method includes determining an index of regularity that exceeds a threshold for each selected pair, the index of regularity indicating an approximate congruence of the plurality of coordinate pairs between the first cardiac signal and the different second cardiac signal.

The method further includes constructing a matrix of indexes of regularity for the selected pairs and determining one or more sources of the cardiac rhythm disorder using the matrix of indexes. The method also includes treating cardiac tissue at the one or more sources to suppress or eliminate the cardiac rhythm disorder. In order to treat the cardiac tissue, the method includes delivering one or more of ablation, electrical energy, mechanical energy, drugs, cells, genes and biological agents to the cardiac tissue at the one or more sources.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments are illustrated by way of example and not limitation in the figures of the accompanying drawings in which:

FIG. 4A-4E illustrate an example method of identifying a source of a heart rhythm disorder based on periodic repeating activity of signals at adjacent or distant sensor locations (spatial phase lock) in the heart illustrated in FIG. 1;

DETAILED DESCRIPTION

A system and method for identifying the sources of heart rhythm disorders are disclosed herein. In the following description, for the purposes of explanation, numerous specific details are set forth in order to provide a thorough understanding of example embodiments. It will be evident, however, to one skilled in the art, that an example embodiment may be practiced without all of the disclosed specific details.

Figure 1:
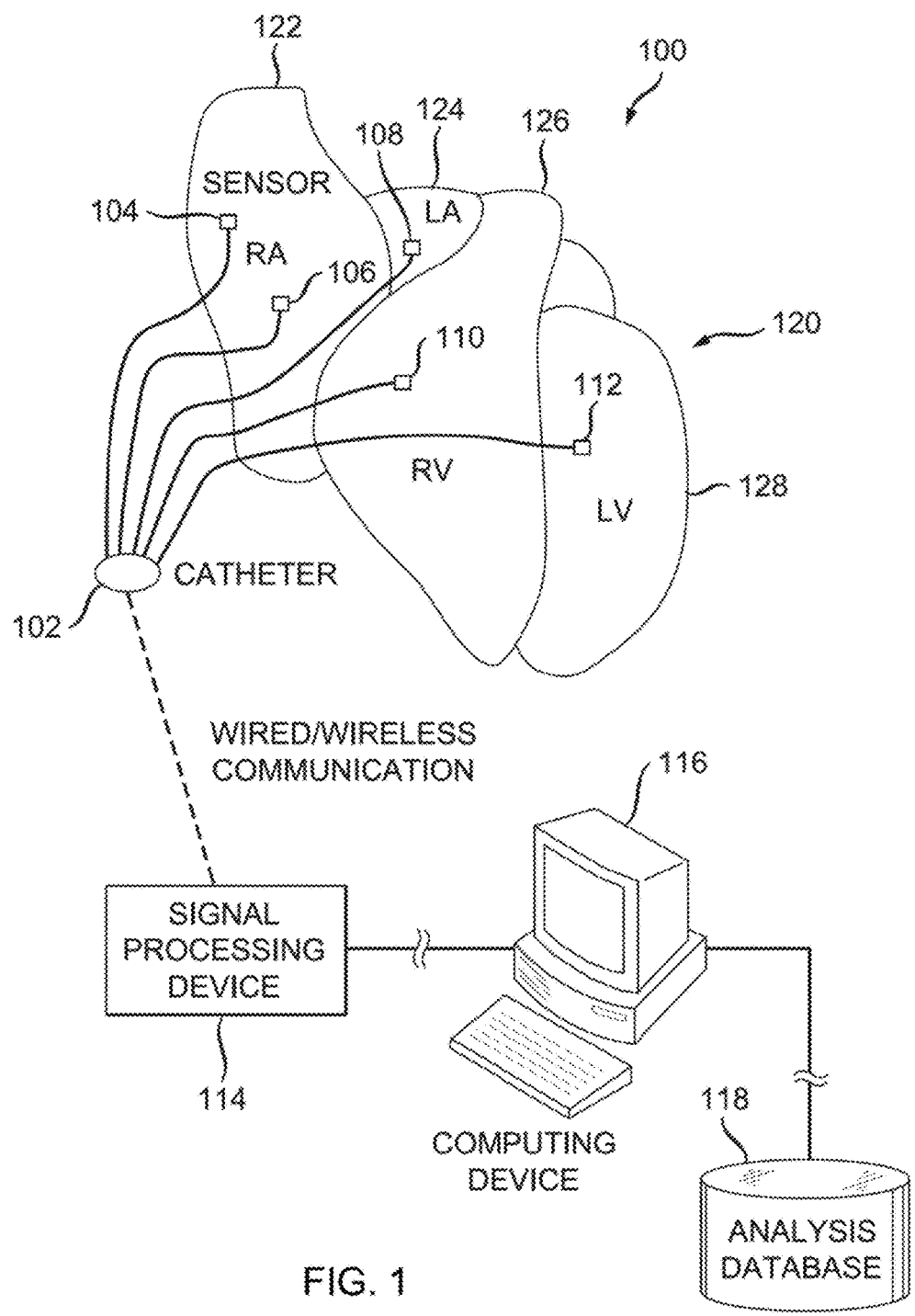
FIG. 1 illustrates an example system to identify a source (or sources) of a heart rhythm disorder.

FIG. 1 illustrates an example system 100 to identify a source (or sources) of a heart rhythm disorder. Specifically, the example system 100 is configured to detect cardiac information (signals) collected/detected from a patient's heart in connection with a heart rhythm disorder. The system 100 is further configured to process the signals in order to determine a region (or multiple regions) of tissue in the patient's heart associated with a specific degree of regularity that exceeds a threshold and differs than a degree of regularity of a plurality of adjacent regions of tissue in the patient's heart. The region (or multiple regions) thus determined indicates a source(s) of the heart rhythm disorder. The heart 120 includes a right atrium 122, left atrium 124, right ventricle 126 and left ventricle 128.

The example system 100 includes a catheter 102, signal processing device 114, computing device 116 and analysis database 118.

The catheter 102 is configured to detect cardiac activation information in the heart and to transmit the detected cardiac activation information to the signal processing device 114, via a wireless connection, wired connection, or a combination of both wired and wireless connections. The catheter includes a plurality of probes/sensors 104-112, which can be inserted into the heart through the patient's blood vessels.

In some embodiments, one or more of the sensors 104-112 may not be inserted into the patient's heart. For example, some sensors may detect cardiac activation via the patient's surface (e.g., electrocardiogram—ECG) or remotely without contact with the patient (e.g., magnetocardiogram). As another example, some sensors may also derive cardiac activation information from cardiac motion of a non-electrical sensing device (e.g., echocardiogram). In various embodiments, these sensors can be used separately or in different combinations, and further these separate or different combinations can also be used in combination with sensors inserted into the patient's heart.

The sensors 104-112, which are positioned at sensor locations in the heart under consideration, can detect cardiac activation information at the sensor locations and can further deliver energy to ablate the heart at the sensor locations. It is noted that the sensors 104-112 can also detect cardiac activation information from overlapping regions of the heart (e.g., right atrium 122 and left atrium 124).

The signal processing device 114 is configured to process (e.g., clarify and amplify) the cardiac activation information detected by the sensors 104-112 at the sensor locations into electrogram signals and to provide the processed signals to the computing device 116 for analysis in accordance with methods disclosed herein. In processing the cardiac activation information from the sensors 104-112, the signal processing device 114 can subtract cardiac activation information from overlapping regions of the heart 120 to provide processed signals to the computing device 116 for analysis. While in some embodiments, the signal processing device 114 is configured to provide unipolar signals, in other embodiments, the signal processing device 114 can provide bipolar signals.

The computing device 116 is configured to receive detected/processed signals from the signal processing device 114 and further configured to analyze the signals in accordance with methods disclosed herein to determine regularity in adjacent regions of the patient's heart, such that it is possible to generate a map(s) (representation(s)) of regularity that can be used to locate a source(s) of the heart rhythm disorder and to eliminate the source(s).

The analysis database 118 is configured to support or aid in the analysis of the signals by the computing device 116. In some embodiments, the analysis database 118 can store the map of regularity associated with or generated on the basis of signals at a plurality of adjacent sensor locations over a period of time, as will be described in greater detail herein. The analysis database 118 can also provide storage of intermediate data associated with the map of regularity.

Figure 2:
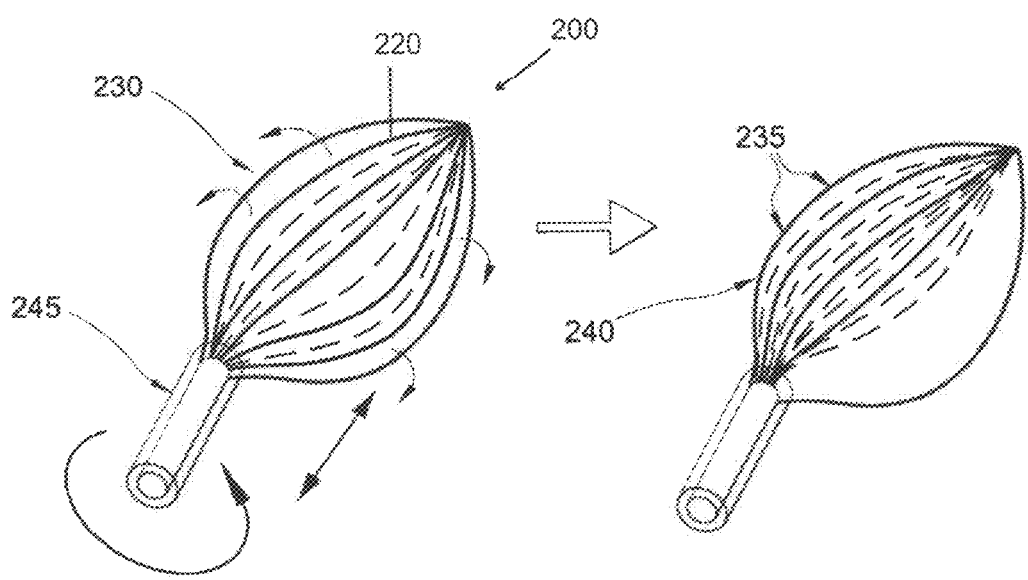
FIG. 2 illustrates an example catheter that can be used to identify the source of a heart rhythm disorder in FIG. 1.

FIG. 2 illustrates an example catheter 200 to detect electrical signals via a plurality of sensors 240 at sensor locations in the heart 120 under consideration. Catheter 200 can be similar to or different than catheter 102 and sensors 240 can be similar to or different than sensors 104-112 in FIG. 1.

The catheter 200 includes multiple splines (or meridians) 220 each of which can include multiple sensors (or probes) 240. By rotating along a shaft axis 245, the splines or meridians 220 may be spaced or separated more widely spatially as depicted at 230 or spaced more closely spatially as depicted at 235.

Different spatial arrangements of the sensors 240 (via spatial separation of the splines 220) can have the effect of spatially extending the area of the heart 120 under consideration. The sensors 240 positioned in a spatial arrangement at sensor locations of the heart 120 under consideration can detect cardiac electrical signals at the sensor locations and can further deliver energy to ablate (or other treatment to treat) the heart at the sensor locations.

Different catheters with various spatial arrangements of the sensors 240 can be used, such as spiral, radial spokes or other spatial arrangements.

Figure 3A:
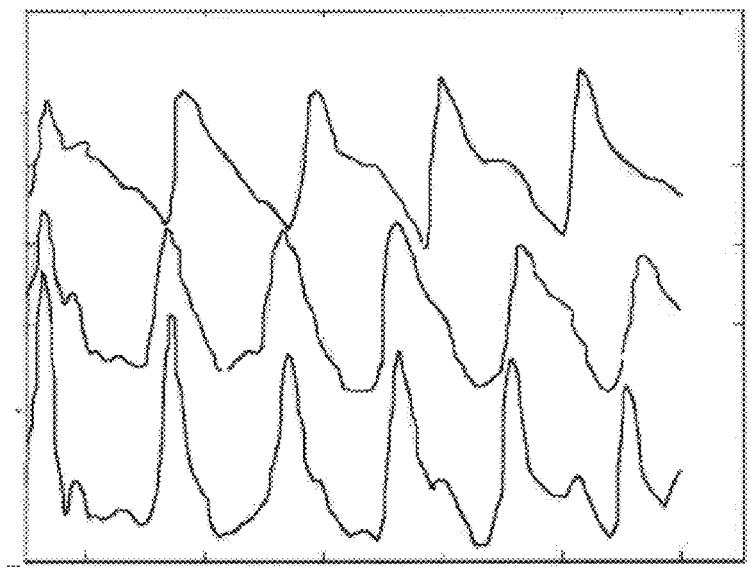
FIGS. 3A-B illustrate an example simple electrogram signal of a heart rhythm disorder and a complex electrogram signal of a heart rhythm disorder from sensors positioned at sensor locations in a heart illustrated in FIG. 1.

FIG. 3A illustrates an example of simple electrocardiogram signals of a heart rhythm disorder from sensors positioned at sensor locations in the heart 120.

In this example, the signals generally show identifiable activation onsets (e.g., for heart beats). The heart beats can be characterized by an activation onset with a sharp inflection point and high slope representing depolarization, followed by a period of gentle, low-deviation slope representing repolarization, typically lasting between about 100 ms and 250 ms.

The regularity or phase relationship between the simple signals in FIG. 3(A) is generally easily identifiable.

Figure 3B:
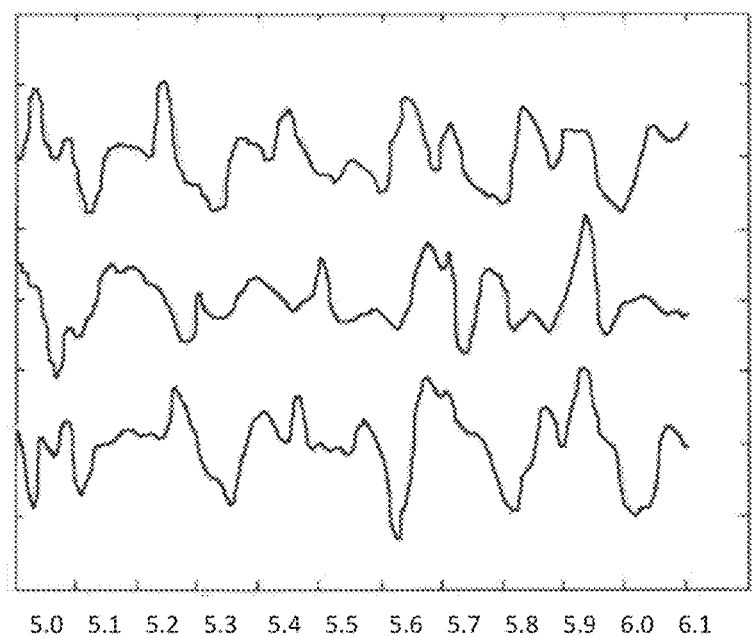

FIG. 3B illustrates an example of complex electrocardiogram signals of a heart rhythm disorder from sensors positioned at sensor locations in the heart 120. As an example, the heart rhythm disorder can be a complex rhythm disorder AF, VF and polymorphic VT, or another heart rhythm disorder.

The signals in FIG. 3B do not generally show identifiable activation onsets (e.g., for heart beats). The signals include multiple deflections of short duration caused by the heart rhythm disorder that makes the discernment of activation onsets (depolarization) prohibitively difficult. Similarly, regularity or phase relationship between complex signals in FIG. 3B is not easily discerned.

FIGS. 4A-4E illustrate an example method of identifying a source of a heart rhythm disorder based on periodic repeating activity (regularity) of signals at adjacent (or distant) sensor locations (e.g., spatial phase lock) in the heart 120 illustrated in FIG. 1.

FIG. 4A illustrates three (3) example signals (e.g., ECG signals) obtained from three adjacent sensor locations (sites 1, 2 and 3) in the heart 120 of FIG. 1, such as via electrodes in the catheter 102, 200. It is noted that multiple signals can be considered from the catheter 102, 200, e.g., 64, 128, or another number of signals. Each of the signals is a voltage time series. The three signals have varying amplitudes (e.g., voltage) along the signals as detected by the sensors of the catheter 102, 200. Four example time points ("A", "B", "C" and "D") are illustrated in the signals for clarity and brevity in describing the processing of the signals in accordance with the example method as described below. However, it is to be noted that there is a multiplicity of time points along each of the example signals that can be processed in accordance with the example methods disclosed herein.

In accordance with the example method, a derivative of each signal is determined at the plurality of time points. The derivative can be a zero order derivative or a higher-order derivative (e.g., a first-order derivative or second-order derivative). For example, a derivative of the first (analysis) cardiac signal is determined at a plurality of first time points (e.g., A, B, C and D). As another example, a derivative of the second (reference) cardiac signal is determined at a plurality of second time points (e.g., A, B, C and D). Similarly, a derivative of the third cardiac signal is determined at a plurality of third time points (e.g., A, B, C and D). In some embodiments, the pluralities of time points in the different signals are contemporaneous. It is again noted that the signals include a multiplicity of time points that can be processed in accordance with the example methods as described herein.

In FIG. 4B, the derivative of the first (analysis) cardiac signal at the plurality of first time points is processed against the derivative of the second (reference) cardiac signal at the plurality of second time points to define a plurality of coordinate pairs of the first cardiac signal against the second cardiac signal. These coordinate pairs can be maintained in memory and/or saved to database 118. In some embodiments, the plurality of coordinate pairs associated with processing of the first cardiac signal against the second cardiac signal can be plotted and connected to generate a plurality of loops. For example, the coordinate pairs associated with example time points A-D can be plotted and connected to generate a first loop, as shown in left panel of FIG. 4B.

Further with reference to FIG. 4B, the plotting and connecting can be repeated for a plurality of first and second time points to generate multiple loops as shown in right panel of FIG. 4B. In this example, a single loop is shown in the left panel of FIG. 4B, based on time points A-D for illustrative purposes. The single loop can represent a single cycle of a heart rhythm, while multiple loops can represent multiple cycles of the heart rhythm. As illustrated, a high degree of regularity (or phase relationship) is observed among the loops shown in the right panel of FIG. 4B. It is noted that the same processing can be repeated for the first (analysis) cardiac signal against different second (reference) cardiac signals, i.e., others of the adjacent 64 or 128 signals.

In FIG. 4C, the derivative of the second (analysis) cardiac signal at the plurality of first time points is processed against the derivative of the third (reference) cardiac signal at the plurality of third time points to define a plurality of coordinate pairs of the second cardiac signal against the third cardiac signal. These coordinate pairs can be maintained in memory and/or saved to database 118. In some embodiments, the plurality of coordinate pairs associated with processing of the second cardiac signal against the third cardiac signal can be plotted and connected to generate a plurality of loops. It is noted that the same processing can be repeated for the second (analysis) cardiac signal against different third (reference) cardiac signals, i.e., others of the adjacent 64 or 128 signals.

Further with reference to FIG. 4C, the plotting and connecting can be repeated for a plurality of second and third time points to generate multiple loops as shown in right panel of FIG. 4C. In this example, a single loop is shown in left panel of FIG. 4C based on time points A-D for illustrative purposes. The single loop can represent a single cycle of a heart rhythm, while multiple loops can represent multiple cycles of the heart rhythm. As illustrated, a low degree of regularity (or phase relationship) is observed amongst the loops in the right panel of FIG. 4C.

In FIG. 4D, an index of regularity is determined with respect to the first cardiac signal (analysis signal) against the second (reference) cardiac signal. The index of regularity indicates an approximate congruence (e.g., mathematical congruence) of the plurality of coordinate pairs between the first cardiac signal and the second cardiac signal. The index of regularity can be determined in one of a time domain, frequency domain and spatial domain. A further determination can be made as to whether the index of regularity of FIG. 4D, exceeds a threshold. In some embodiments, the threshold can be defined to indicate an upper percentile (e.g., top $5^{th}$ percentile) of all indexes of regularity of the first (analysis) cardiac signal against second (reference) cardiac signals, i.e., the adjacent eight (8) signals, repeated for signals from 64 or 128 sensor locations. A different percentile may be used, e.g., $10^{th}$ percentile, or another percentile number.

With reference to the frequency domain, a frequency analysis (e.g., Fourier analysis) can be performed using a selected parameter associated with the plurality of coordinate pairs (or loops) to generate a frequency spectrum, as shown in FIG. 4D. The selected parameter can be amplitude (e.g., voltage), angle, vector, area and derivative. Thereafter, at least one peak is determined in the frequency spectrum of FIG. 4D. In some embodiments, the at least one peak can include a fundamental frequency. In other embodiments, the at least one peak can include the fundamental frequency and also one or more harmonics of the fundamental frequency. In still other embodiments, the at least one peak can include only one or more of the harmonics of the fundamental frequency, i.e., the fundamental frequency can be excluded.

In performing the frequency analysis, a sum of the area of the at least one peak in the frequency spectrum in FIG. 4D is calculated. A result (i.e., index of regularity) is calculated by dividing the sum of the area of the at least one peak by a total area of the frequency spectrum within a predefined frequency range, such as between about 4 Hz and about 12 Hz. In some embodiments, other frequency ranges can be defined. Thereafter, it can be determined whether the result (index of regularity) exceeds the threshold, such as an upper percentile (e.g., top $5^{th}$ percentile) of all indexes of regularity of the first (analysis) cardiac signal against second (reference) cardiac signals, i.e., the adjacent eight (8) signals, repeated for signals from 64 or 128 sensor locations. For example, the index of regularity for the loops of FIG. 4B as shown in FIG. 4D is 0.178, indicating a high degree of regularity (or phase relationship) of the first cardiac signal against the second cardiac signal. In frequency analysis, the index of regularity will be in a range between about 0.0 and about 1.0.

In FIG. 4E, an index of regularity is determined with respect to the second (analysis) cardiac signal against the third (reference) cardiac signal. The index of regularity indicates an approximate congruence (e.g., mathematical congruence) of the plurality of coordinate pairs between the second cardiac signal and the third cardiac signal. As described previously, the index of regularity can be determined in one of a time domain, frequency domain and spatial domain. A further determination can be made as to whether the index of regularity of FIG. 4E exceeds a threshold. In some embodiments, the threshold can be defined to indicate an upper percentile (e.g., top $5^{th}$ percentile) of all indexes of regularity of the second (analysis) cardiac signal against third (reference) cardiac signals, i.e., the adjacent eight (8) signals, repeated for signals from 64 or 128 sensor locations. Similarly, a different percentile can be used, e.g., $10^{th}$ percentile, or anther percentile number.

Moreover, a frequency analysis (e.g., Fourier analysis) can be performed using a selected parameter associated with the plurality of coordinate pairs (or loops) to generate a frequency spectrum, as shown in FIG. 4E. The selected parameter can be amplitude (e.g., voltage), angle, vector, area and derivative. Thereafter, at least one peak can be determined in the frequency spectrum of FIG. 4E. In some embodiments, the at least one peak can include a fundamental frequency. In other embodiments, the at least one peak can include the fundamental frequency and also one or more harmonics of the fundamental frequency. In still other embodiments, the at least one peak can include only one or more of the harmonics of the fundamental frequency, i.e., the fundamental frequency can be excluded.

In performing the frequency analysis, a sum of the area of the at least one peak in the frequency spectrum of FIG. 4E is calculated. A result (i.e., index of regularity) is calculated by dividing the sum of the area of the at least one peak by a total area of the frequency spectrum within a predefined frequency range, such as between about 4 Hz and about 12 Hz. In some embodiments, other frequency ranges can be defined. Thereafter, it can be determined whether the result (index of regularity) exceeds the threshold, i.e., an upper percentile (e.g., top $5^{th}$ percentile) of all indexes of regularity of the first (analysis) cardiac signal against second (reference) cardiac signals, i.e., the adjacent eight (8) signals, repeated for signals from 64 or 128 sensor locations. For example, the index of regularity for the loops of FIG. 4C as shown in FIG. 4E is 0.073, indicating a low degree of regularity (or phase relationship) of the second cardiac signal against the third cardiac signal.

The congruence (regularity or phase relationship) of the signals can be quantified over time by using a selected parameter(s) or characteristic(s) (e.g., angles, vectors, amplitudes, areas, derivatives, and/or other characteristc(s)) and quantifying regularity associated with the selected parameter(s) using a FFT (Fourier transform) in excess of a threshold. FIG. 4B shows the congruence (regularity or phase relationship) between the first cardiac signal and the second cardiac signal. In FIG. 4D, the discrete peaks of the FFT reflect regularity in excess of the threshold. FIG. 4C shows the lack of congruence (regularity or phase relationship) between the second cardiac signal and the third cardiac signal. In FIG. 4E, the FFT does not show discrete peaks in excess of the threshold, reflecting significant variability between the second cardiac signal and the third cardiac signal.

Figure 5:
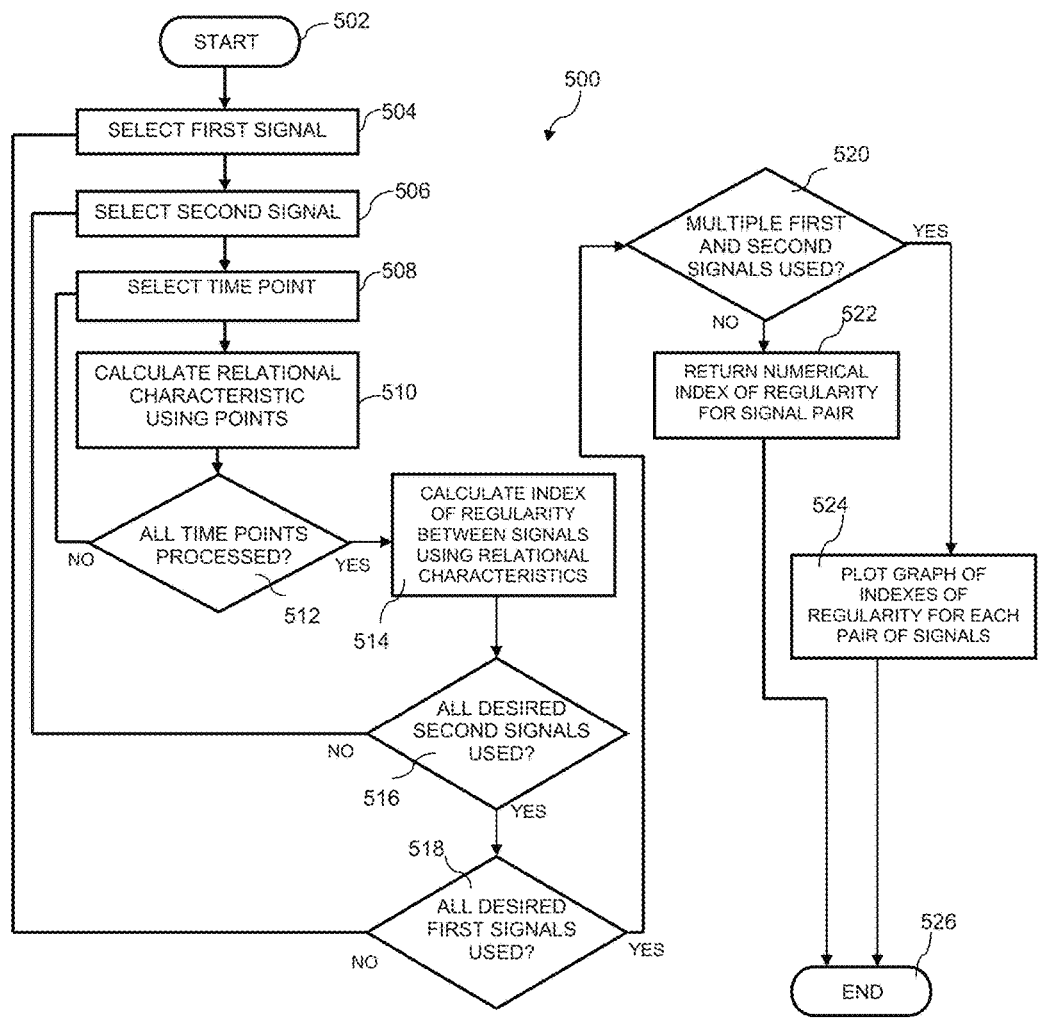
FIG. 5 is a flowchart that illustrates an example method of determining periodic repeating activity (spatial phase lock) to identify a source of a heart rhythm disorder.

FIG. 5 is a flowchart that illustrates an example method 500 of determining periodic repeating activity (spatial phase lock) to identify a source of a heart rhythm disorder. The method starts at operation 502. At operations 504, 506, a pair of cardiac signals is selected form a plurality of cardiac signals. Specifically, at operation 504 a first (analysis) signal is selected from the plurality of signals and at operation 506 a second (reference) signal is selected from the plurality of signals. As described herein, there can be 64, 128, or another number of signals. The signals can be ECG signals processed via signal processing device 114 of FIG. 1.

At operation 508, a time point is selected with reference to the processing of the first cardiac signal with respect to the second cardiac signal. At operation 510, a relational characteristic(s) is calculated using the time point. This characteristic(s) can be stored, such as in database 118. The characteristic(s) can identify the relationship between the time points. For example, a derivative of each signal can be determined at the selected time point. Specifically, a derivative of the first cardiac signal can be processed against a derivative of the second cardiac signal at the selected time point to define a coordinate pair of the first cardiac signal against the second cardiac signal.

At operation 512, a determination is made as to whether all time points have been processed. If it is determined that all time points have not been processed, the method continues to perform operations 508-512 until all time points have been processed. If it is determined that all time points have been processed, the method 500 continues at operation 514.

At operation 514, an index of regularity is computed between the selected signals using the relational characteristic(s). At operation 516, it is determined whether all desired second (reference) signals have been used in relation to the selected first (analysis) signal. If it is determined that all desired second signals have not been used, the method 500 continues at operations 506-516 until all desired second signals have been used in relation to the first selected signal. In some embodiments, the coordinate pairs associated with processing of the first (analysis) cardiac signal against all the second (reference) cardiac signals at the plurality of time points can be plotted and connected to generate a plurality of loops, as shown in example right panel of FIG. 4B.

If it is determined that all desired second signals have been processed, the method 500 continues at operation 518 where it is determined whether all desired first (analysis) signals have been used. If it is determined that all desired first signals have not been used, the method 500 continues at operations 504-516 until all desired first signals have been used.

At operation 520, it is determined whether multiple first and multiple second signals were used. If it is determined that multiple signals were not used, then at operation 522 an index of regularity can be returned for the selected first and second signals. However, if it is determined that multiple first signals and multiple second signals were used, then at operation 524 a graph (map) of indexes of regularity can be generated for each pair of first and second signals. (See the map in FIG. 7). In some embodiments, the indexes of regularity can be maintained in memory and/or stored in database 118. A determination can be made to identify (or indicate) one or more indexes of regularity that exceed a threshold. As described previously, the threshold can be defined to indicate an upper percentile (e.g., top $5^{th}$ percentile) of all indexes of regularity of the first (analysis) cardiac signal against second (reference) cardiac signals, i.e., of the adjacent 64 or 128 signals. Similarly, a different percentile can be used, e.g., $10^{th}$ percentile, or anther percentile number. Those indexes of regularity for signals exceeding the threshold (e.g., within the top 5$^{th}$ percentile), which surround adjacent indexes of regularity for signals not exceeding the threshold, can be used to indicate the source of the cardiac rhythm disorder. The method ends at operation 526.

Figure 6A:
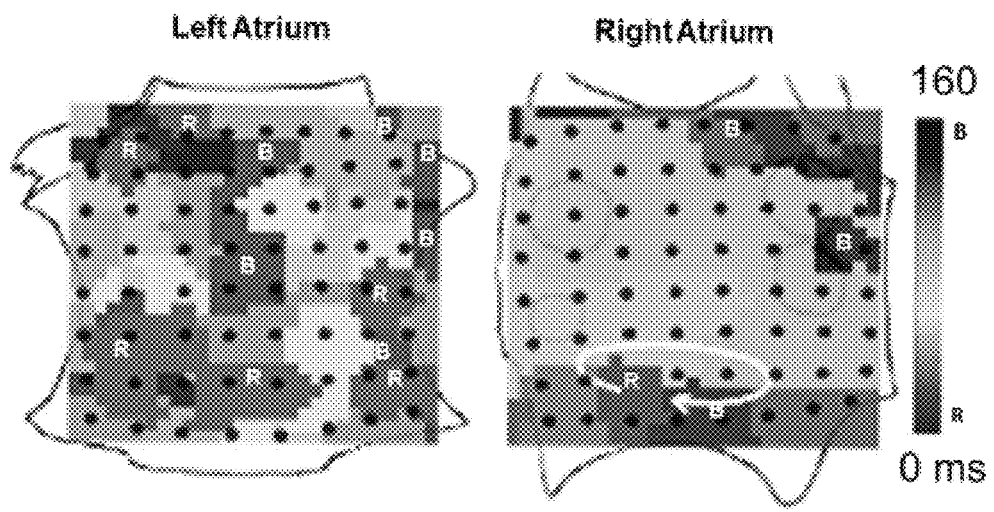
FIG. 6A-6E illustrate example migration of a source (locus) of a heart rhythm disorder and the use of spatial phase lock to identify such a source of heart rhythm disorder.
Figure 6B:
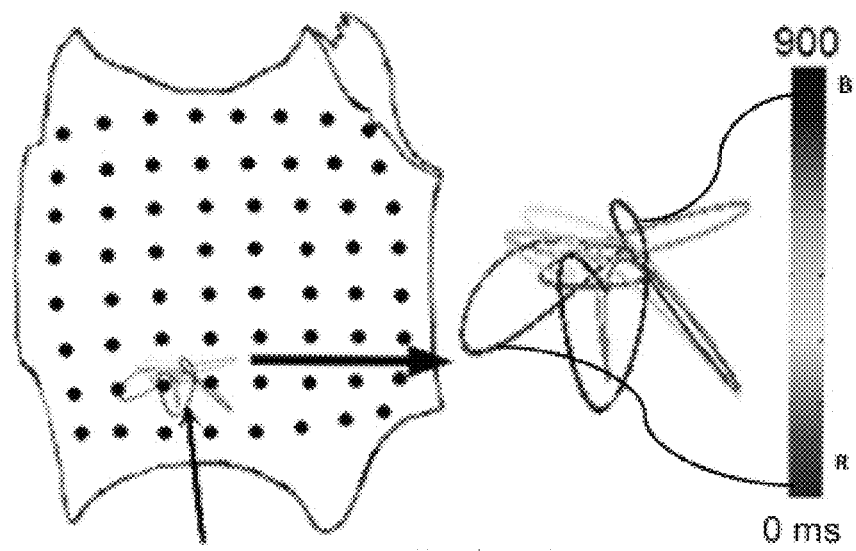
Figure 6C:
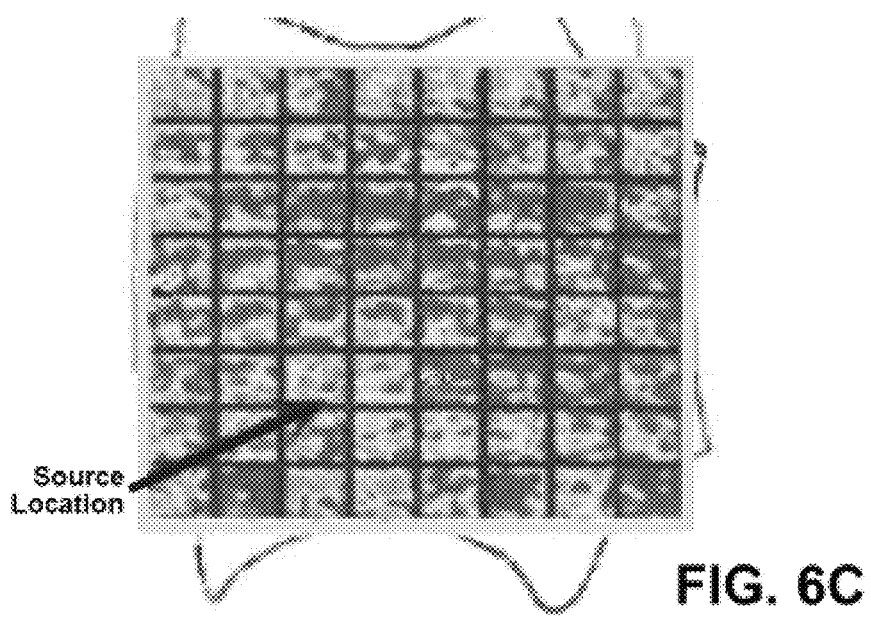
Figure 6D:
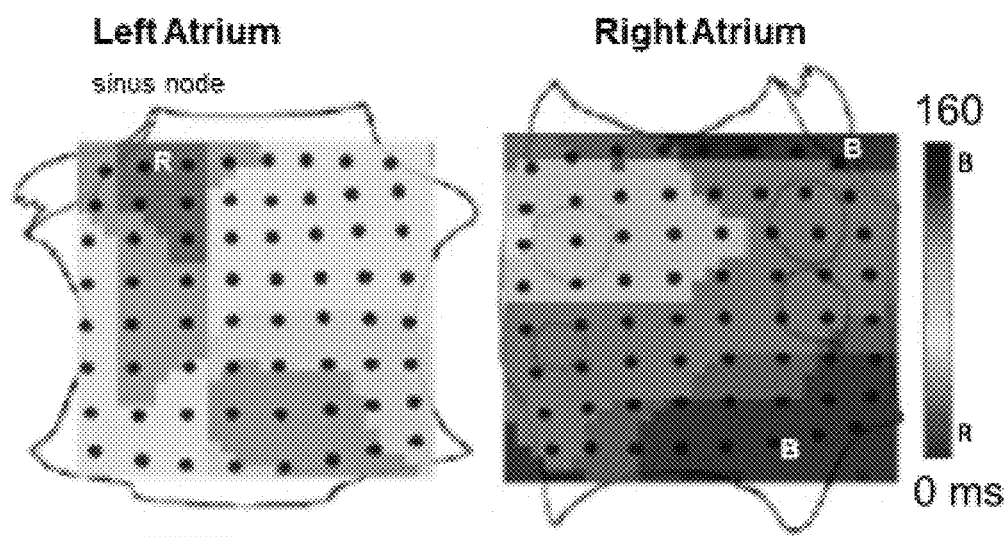
Figure 6E:
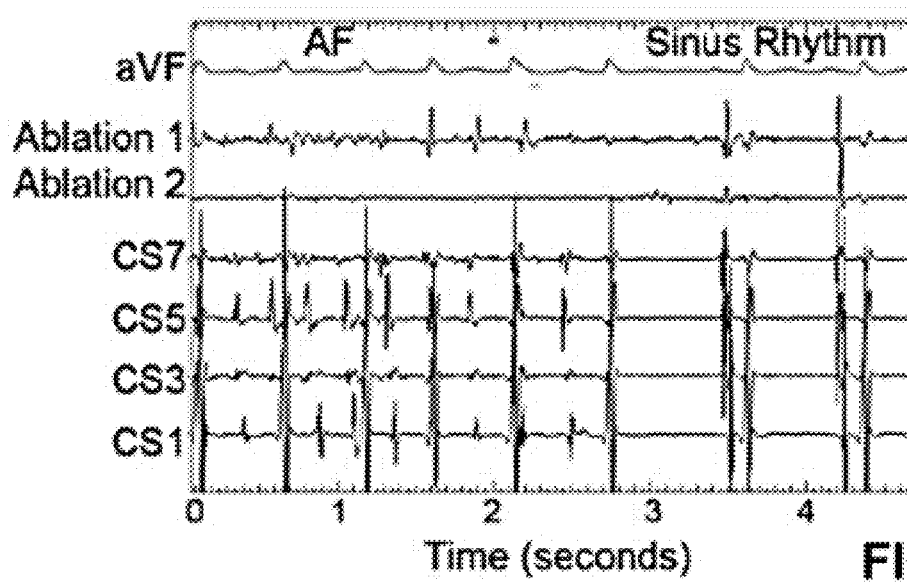

FIGS. 6A-6E illustrate example migration of a source (locus) of a heart rhythm disorder and the use of indexes of regularity (e.g., spatial phase lock) to identify such a source of heart rhythm disorder in a patient. Specifically, FIGS. 6A-6E show AF termination by ablation of the source for human atrial fibrillation identified by the indexes of regularity (e.g., spatial phase lock). In FIG. 6A, left atrial rotational source during AF is visualized using contours of activation time (e.g., isochrones), where the activation times for a 160 ms period of time are color-coded from red ("R") at about 0 ms to blue ("B") at about 160 ms. FIG. 6B shows the locus of migration of the source shown in FIG. 6A for a 900 ms time period. In FIG. 6C, indexes of regularity (e.g., spatial phase lock) illustrate a region of low regularity (cool colors, indicated by the arrow) relative to and surrounded by adjacent regions of high regularity (warmer colors). This region is a source of the cardiac rhythm disorder and agrees precisely with the rotational source in FIG. 6A. As shown on patient specific geometry in FIG. 6C, the source for AF is in the low left atrium. In FIG. 6D, electrode signals are shown during AF with termination to sinus rhythm by <1 minute after ablation at the region of high regularity around the region of low regularity (i.e., rotational source in FIG. 6A) (ECG lead aVF, and electrodes at ablation catheter, coronary sinus). In FIG. 6E, an isochronal map of the sinus rhythm is shown for the referenced patient. This patient remains free of AF on implanted cardiac monitor. (Scale Bar 1 cm).

Figure 7:
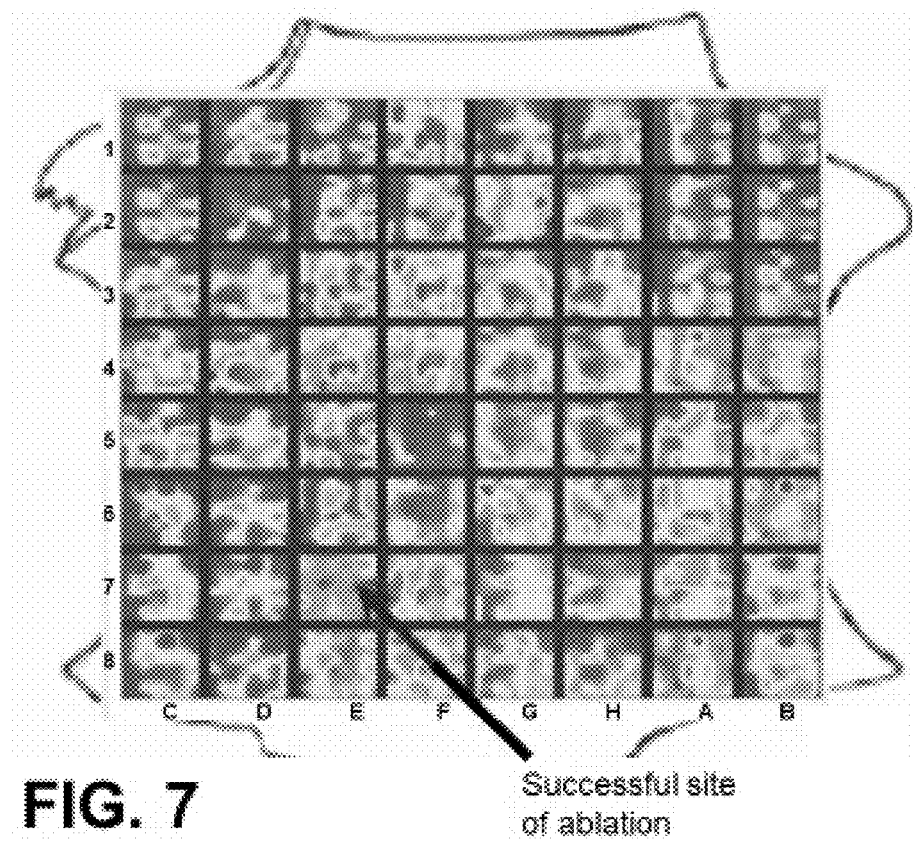
FIG. 7 illustrates an example map of indexes of periodic repeating activity (regularity) to identify a source of heart rhythm disorder.

FIG. 7 illustrates an example map of indexes of regularity to identify a source of heart rhythm disorder.

The map of indexes of regularity for each signal processed can be generated as a grid of sub-maps, with each sub-map showing the index of regularity using a different first (analysis) signal and every second (reference) signal processed against the first signal. Thereafter, a map can be generated as a combination of sub-maps. The map arranges each signal in an approximate spatial relationship with the other signals. A color is assigned to a pixel at each sensor location representing a value of the index of regularity for the signal pair (e.g., higher values coded in red, lower values in blue). Each first (analysis) signal's sub-map can then be placed into the larger map that represents that first signal's spatial location with the other processed first (analysis) signals, creating an 8×8 map as shown in FIG. 7.

As shown in FIG. 7, a region of high regularity (warm colors) that surrounds an adjacent region of low regularity (cool colors) can be determined. The black arrow points to a site of successful ablation on or within the region of high regularity. Similarly, a region of low regularity that is surrounded by a region of high regularity can also be determined for ablation to eliminate the source of the cardiac rhythm disorder.

Figure 8:
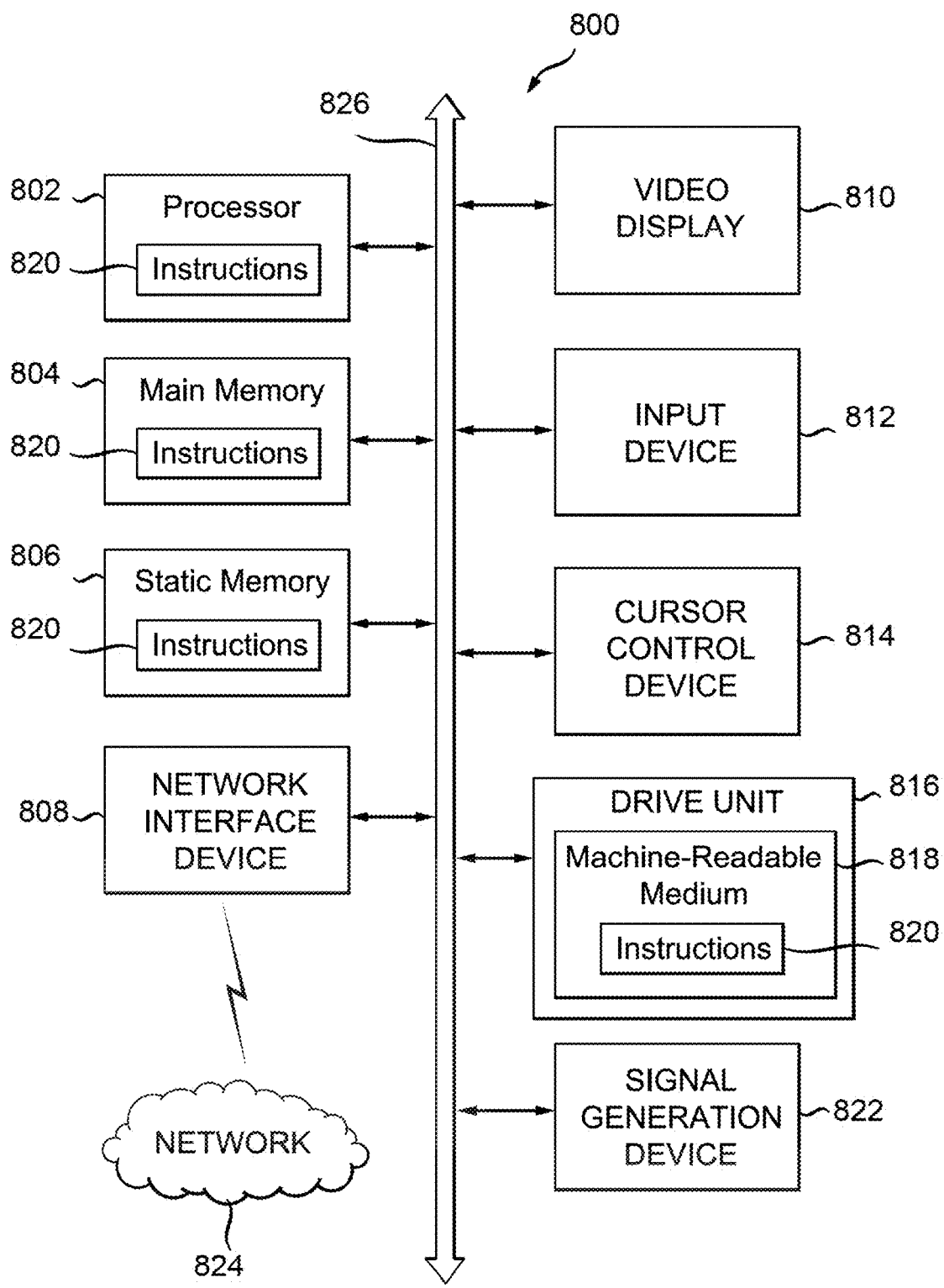
FIG. 8 is a block diagram of an illustrative embodiment of a general computer system.

FIG. 8 is a block diagram of an illustrative embodiment of a general computer system 800. The computer system 800 can be the signal processing device 114 and the computing device 116 of FIG. 1. The computer system 800 can include a set of instructions that can be executed to cause the computer system 800 to perform any one or more of the methods or computer based functions disclosed herein. The computer system 800, or any portion thereof, may operate as a standalone device or may be connected, e.g., using a network or other connection, to other computer systems or peripheral devices. For example, the computer system 800 may be operatively connected to signal processing device 114 and analysis database 118.

In operation as described in FIGS. 1-7, the identification of source(s) of heart rhythm disorders as described herein can be used to identify patients in whom therapy can be effective and to assist in guiding such therapy, which can include delivery of one or more of ablation, electrical energy, mechanical energy, drugs, cells, genes and biological agents to at least a portion of the identified source(s) of the heart.

The computer system 800 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 800 is illustrated, the term "system" shall also be taken to include any collection of systems or sub-systems that individually or jointly execute a set, or multiple sets, of instructions to perform one or more computer functions.

As illustrated in FIG. 8, the computer system 800 may include a processor 802, e.g., a central processing unit (CPU), a graphics-processing unit (GPU), or both. Moreover, the computer system 800 may include a main memory 804 and a static memory 806 that can communicate with each other via a bus 826. As shown, the computer system 800 may further include a video display unit 810, such as a liquid crystal display (LCD), an organic light emitting diode (OLED), a flat panel display, a solid state display, or a cathode ray tube (CRT). Additionally, the computer system 800 may include an input device 812, such as a keyboard, and a cursor control device 814, such as a mouse. The computer system 800 can also include a disk drive unit 816, a signal generation device 822, such as a speaker or remote control, and a network interface device 808.

In a particular embodiment, as depicted in FIG. 8, the disk drive unit 816 may include a computer-readable medium 818 in which one or more sets of instructions 820, e.g., software, can be embedded. Further, the instructions 820 may embody one or more of the methods or logic as described herein. In a particular embodiment, the instructions 820 may reside completely, or at least partially, within the main memory 804, the static memory 806, and/or within the processor 802 during execution by the computer system 800. The main memory 804 and the processor 802 also may include computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments, the methods described herein may be implemented by software programs tangibly embodied in a processor-readable medium and may be executed by a processor. Further, in an exemplary, non-limited embodiment, implementations can include distributed processing, component/object distributed processing, and parallel processing. Alternatively, virtual computer system processing can be constructed to implement one or more of the methods or functionality as described herein.

It is also contemplated that a computer-readable medium includes instructions 820 or receives and executes instructions 820 responsive to a propagated signal, so that a device connected to a network 824 can communicate voice, video or data over the network 824. Further, the instructions 820 may be transmitted or received over the network 824 via the network interface device 808.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, a system and method to reconstruct cardiac activation information have been described. Although specific example embodiments have been described, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of any of the above-described embodiments, and other embodiments not specifically described herein, may be used and are fully contemplated herein.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

The invention claimed is:

1. A method of determining regularity associated with a source of a cardiac rhythm disorder, the method comprising:
processing by a computing device one of a zero order, a first order, and a higher order derivative of a first cardiac signal associated with a first location at a plurality of first time points against one of a zero order, a first order, and a higher order derivative of a second cardiac signal associated with a second location at a plurality of second time points to define a plurality of coordinate pairs of the first cardiac signal against the second cardiac signal;
determining by the computing device an index of regularity that exceeds a threshold, the index of regularity being associated with periodic repeating activity, the index of regularity indicating an approximate congruence of the plurality of coordinate pairs among the first cardiac signal and the second cardiac signal;

iteratively selecting pairs of cardiac signals from the plurality of defined coordinate pairs of cardiac signals;

performing the processing and determining for each pair of the iteratively selected pairs of cardiac signals;

constructing a matrix of indexes of regularity for the iteratively selected pairs of cardiac signals; and determining one or more sources of the rhythm disorder using the matrix of indexes of regularity.

2. The method of claim 1, wherein determining the one or more sources comprises:

identifying from the matrix one or more regions of the heart associated with higher indexes of regularity as compared to indexes of regularity at adjacent regions of the heart.

3. The method of claim 1, wherein the first cardiac signal and the second cardiac signal are from different regions of the heart.

4. The method of claim 1, wherein the plurality of first time points is contemporaneous with the plurality of second time points.

5. The method of claim 1, wherein the method further comprises:

plotting the plurality of coordinate pairs; and connecting the plurality of coordinate pairs to generate a plurality of loops.

6. The method of claim 5, wherein the index of regularity indicates the approximate congruence among the plurality of loops.

7. The method of claim 1, wherein the method further comprises:

performing a frequency analysis using a selected parameter associated with the plurality of coordinate pairs to generate a frequency spectrum; and determining at least one peak in the frequency spectrum.

8. The method of claim 7, further comprising:

calculating a sum of the area of the at least one peak in the frequency spectrum;

calculating a result from dividing the sum of the area of the at least one peak by a total area of the frequency spectrum within a predefined frequency range; and determining whether the result exceeds the threshold.

9. The method of claim 7, wherein the at least one peak includes a fundamental frequency.

10. The method of claim 9, wherein the at least one peak further includes one or more harmonics of the fundamental frequency.

11. The method of claim 7, wherein the at least one peak includes one or more harmonics of a fundamental frequency.

12. The method of claim 7, wherein the selected parameter is one of amplitude, angle, vector, area and derivative.

13. The method of claim 7, wherein the frequency analysis is a Fourier analysis.

14. The method of claim 1, wherein the one of a zero order, a first order, and a higher order derivative of the first cardiac signal and the one of a zero order, a first order, and a higher order derivative of the second cardiac signal are one of a first order derivative and a higher order derivative.

15. The method of claim 1, wherein the one of a zero order, a first order, and a higher order derivative of the first cardiac signal and the one of a zero order, a first order, and a higher order derivative of the second cardiac signal are a zero order derivative.

16. The method of claim 1, wherein one of the first order and the higher order derivative of the first cardiac signal and one of the first order and the higher order derivative of the second cardiac signal are in one of time and space.

17. The method of claim 1, wherein the index of regularity is determined in one of a time domain, frequency domain and spatial domain.

18. The method of claim 1, wherein the approximate congruence indicates recurrence of at least a portion of the plurality of coordinate pairs within a defined confidence interval.

19. The method of claim 1, wherein the method further comprises iteratively selecting the first cardiac signal and the second cardiac signal from a plurality of cardiac signals.

20. The method of claim 1, wherein the first cardiac signal and the second cardiac signal represent a first voltage time series and a second voltage time series, respectively.

21. The method of claim 1, wherein the plurality of first time points and the plurality of second time points are associated with at least one beat of the rhythm disorder.

22. A system to determine regularity associated with a source of a cardiac rhythm disorder, the system comprising at least one computing device configured to:

process one of a zero order, a first order, and a higher order derivative of a first cardiac signal associated with a first location at a plurality of first time points against s-one of a zero order, a first order, and a higher order derivative of a second cardiac signal associated with a second location at a plurality of second time points to define a plurality of coordinate pairs of the first cardiac signal against the second cardiac signal;

determine an index of regularity that exceeds a threshold, the index of regularity being associated with periodic repeating activity, the index of regularity indicating an approximate congruence of the plurality of coordinate pairs among the first cardiac signal and the second cardiac signal;

iteratively select pairs of cardiac signals from the plurality of defined coordinate pairs of cardiac signals;

perform the processing and determining for each pair of the iteratively selected pairs of cardiac signals;

construct a matrix of indexes of regularity for the iteratively selected pairs of cardiac signals; and determine one or more sources of the cardiac rhythm disorder using the matrix of indexes of regularity.

23. The system of claim 22, wherein the at least one computing device is further configured to:

identify from the matrix one or more regions of the heart associated with higher indexes of regularity as compared to indexes of regularity at adjacent regions of the heart.

24. The system of claim 22, wherein the at least one computing device is further configured to iteratively select the first cardiac signal and the second cardiac signal from a plurality of cardiac signals.

25. The system of claim 24, further comprising a catheter that includes a plurality of sensors configured to detect the plurality of cardiac signals.

26. The system of claim 22, further comprising a display device configured to display the index of regularity.

27. The system of claim 22, further comprising a computer storage medium comprising instructions, which when executed by the at least one computing device, cause the at least one computing device to process and determine.

* * * * *